(12) United States Patent
Benson et al.

(10) Patent No.: US 8,403,822 B2
(45) Date of Patent: Mar. 26, 2013

(54) PASSIVE VENT FOR BRACHYTHERAPY BALLOON CATHETERS

(75) Inventors: Maria Benson, West Boylston, MA (US); Donna Allan, Bedford, NH (US); Walter Ocampo, Marlborough, MA (US)

(73) Assignee: Cytyc Corporation, Marlborough, MA (US)

( * ) Notice: Subject to any disclaimer, the term of this patent is extended or adjusted under 35 U.S.C. 154(b) by 874 days.

(21) Appl. No.: 12/389,577

(22) Filed: Feb. 20, 2009

(65) Prior Publication Data

US 2010/0217064 A1 Aug. 26, 2010

(51) Int. Cl.
*A61N 5/00* (2006.01)
(52) U.S. Cl. ............................................. 600/3; 600/1
(58) Field of Classification Search ................. 600/3–8; 128/203.12–204.14; 604/246, 247, 256, 604/533–539
See application file for complete search history.

(56) References Cited

U.S. PATENT DOCUMENTS

| | | | |
|---|---|---|---|
| 3,192,949 A | 7/1965 | De See | |
| 3,385,301 A | 5/1968 | Harautuneian | |
| 3,570,484 A | 3/1971 | Steer | |
| 3,831,629 A | 8/1974 | Mackal | |
| 3,986,508 A * | 10/1976 | Barrington | 604/411 |
| 4,123,091 A * | 10/1978 | Cosentino et al. | 285/39 |
| 4,154,342 A * | 5/1979 | Wallace | 206/439 |
| 4,222,407 A | 9/1980 | Ruschke | |
| 4,246,932 A | 1/1981 | Raines | |
| 4,286,628 A | 9/1981 | Paradis et al. | |
| 4,310,017 A | 1/1982 | Raines | |
| 4,369,812 A | 1/1983 | Paradis et al. | |
| 4,535,820 A | 8/1985 | Raines | |
| 4,610,469 A * | 9/1986 | Wolff-Mooij | 285/260 |
| 4,683,916 A | 8/1987 | Raines | |
| 5,423,791 A | 6/1995 | Bartlett | |
| 5,931,774 A * | 8/1999 | Williams et al. | 600/2 |
| 5,964,261 A | 10/1999 | Neuenfeldt et al. | |
| 6,482,188 B1 | 11/2002 | Rogers et al. | |
| 6,875,205 B2 | 4/2005 | Leinsing | |
| 6,979,323 B2 | 12/2005 | Rogers et al. | |
| 7,306,199 B2 | 12/2007 | Leinsing et al. | |
| 7,319,735 B2 | 1/2008 | Defreitas et al. | |
| 7,520,489 B2 * | 4/2009 | Ruschke et al. | 251/149.7 |

(Continued)

FOREIGN PATENT DOCUMENTS

WO WO 2009027394 A1 * 3/2009

OTHER PUBLICATIONS

"Keeping I.V. therapy safe with needless systems", Nursing, Accessed Jun. 24, 2008.

(Continued)

*Primary Examiner* — Navin Natnithithadha
*Assistant Examiner* — Meredith Weare

(57) ABSTRACT

Embodiments of passive vent valve devices are disclosed. One of the novel aspects of the invention is its ability to transform from a packaging configuration to a use configuration. The packaging configuration allows sterilization gases to penetrate into the device through standard valve openings as well as through vented mesh openings. Passage of gas into the device, in turn, provides a means of sterilizing all surface areas in the device. Alternatively, when the valve is placed in a use configuration, the passage of gas through the vented mesh is inhibited providing a sealed environment that functions as a valve. The invention is useful in manufacturing sterile medical devices by allowing all surfaces to communicate with the sterilizing agent when the valve is in a packaging configuration or when it is in a use configuration.

19 Claims, 2 Drawing Sheets

Configuration in packaging

U.S. PATENT DOCUMENTS

| | | | |
|---|---|---|---|
| 7,803,140 B2 * | 9/2010 | Fangrow, Jr. | 604/256 |
| 7,947,014 B2 * | 5/2011 | Kien | 604/99.02 |
| 2001/0047187 A1 * | 11/2001 | Milo et al. | 606/213 |
| 2002/0019608 A1 | 2/2002 | Mason et al. | 604/133 |
| 2003/0230309 A1 * | 12/2003 | Luchetti et al. | 128/207.15 |
| 2004/0073171 A1 | 4/2004 | Rogers et al. | |
| 2004/0138626 A1 * | 7/2004 | Cote et al. | 604/249 |
| 2004/0143226 A1 * | 7/2004 | Marsden | 604/272 |
| 2004/0158211 A1 | 8/2004 | Rogers et al. | |
| 2005/0101920 A1 * | 5/2005 | Keane et al. | 604/218 |
| 2005/0148994 A1 * | 7/2005 | Leinsing | 604/414 |
| 2005/0245872 A1 * | 11/2005 | Simpson et al. | 604/129 |
| 2005/0273019 A1 * | 12/2005 | Conway et al. | 600/576 |
| 2006/0155258 A1 | 7/2006 | Rogers et al. | |
| 2006/0192164 A1 | 8/2006 | Korogi et al. | |
| 2006/0253090 A1 | 11/2006 | Bradley et al. | |
| 2006/0271015 A1 * | 11/2006 | Mantell | 604/533 |
| 2006/0276770 A1 | 12/2006 | Rogers | |
| 2007/0083162 A1 | 4/2007 | O'Reagan et al. | |
| 2007/0156112 A1 | 7/2007 | Walsh | |
| 2007/0260104 A1 | 11/2007 | Bretz | |
| 2008/0023346 A1 * | 1/2008 | Vonderwalde | 206/210 |
| 2008/0146861 A1 * | 6/2008 | Murphy et al. | 600/3 |
| 2009/0118681 A1 * | 5/2009 | Molgaard-Nielsen | 604/246 |
| 2010/0292640 A1 * | 11/2010 | Kien | 604/99.02 |

OTHER PUBLICATIONS

"Brachytherapy", Radiology Info, Accessed May 28, 2008.
"About Brachytherapy: What is Brachytherapy", American Brachytherapy Society, Accessed May 28, 2008.
"Brachytherapy", Wikipedia the free enclyclopedia, Accessed May 28, 2008.
Material Comparison Chart, Date unknown.
"Overview of Sterilization Procedures", Medical Device Link, Accessed Dec. 22, 2008.
"ETO Sterilization", Medical Device Link, Accessed Nov. 8, 2007.
DuPont Medical Packaging Technical Reference Guide, (Jan. 2007).

* cited by examiner

Passive vent component detail

Injection site / cap detail

Configuration in packaging

Configuration for use

PASSIVE VENT FOR BRACHYTHERAPY BALLOON CATHETERS

FIELD

This patent specification is in the field of medical valves and specifically vented valves for use with brachytherapy balloon catheters.

BACKGROUND

The use of implantable balloons in the treatment of proliferative disorders has become increasingly sophisticated in recent years, and improvements in surgical, chemotherapeutic, and brachytherapeutic techniques have led to better outcomes for patients suffering from such disorders. Treatments for these disorders often include removing a tumor through surgical resection. The surgery is then supplemented with radiation therapy whereby the residual tumor margin is targeted for treatment post resection.

Post resection radiation treatment is often referred to as "brachytherapy" and involves radiation therapy delivered by a spatially-confined source of therapeutic rays inserted into a mammalian body at or near a tumor or other proliferative tissue disease site. Due to the proximity of the radiation source, brachytherapy offers the advantage of delivering a more localized dose to the target tissue region. For example, brachytherapy can be performed by implanting radiation sources directly into the tissue to be treated. In brachytherapy, radiation doses are highest in close proximity to the radiotherapeutic source, providing a high tumor dose while sparing surrounding normal tissue. Brachytherapy is useful for treating malignant brain and breast tumors, among others and is often carried out using radioactive seeds, such as $^{125}I$ or $^{192}Ir$.

In clinical practice, brachytherapy balloons are inflated after insertion in order to occupy the space previously occupied by the resected tumor and allow the radioactive seed to be inserted for the initiation of radioactive brachytherapy. Since brachytherapy devices are inflated for use, a valve is necessary for an interface between the brachytherapy device and numerous medical devices that increase gaseous pressure such as syringes, pumps and tubing that interface with inflationary devices. The valves that form the intersection between these devices may possess one-way or two-way diaphragms or actuation mechanisms. These devices are often needle free valves that permit their safe handling by health care professionals and offer the versatility to interface with various medical devices.

Early types of valve devices used multiple purpose adapters having a valve positioned in the closed position by a spring. The spring in these devices was overridden by insertion of a needleless syringe tip against the valve, overcoming the spring load thus opening the valve. These valves were then used to push fluids or gases into port systems such as brachytherapy balloons as well as bottles, vials, bags and tubing to act as a channel between the port systems. Such valve devices accommodate various uses in supplier containers and hospital settings.

The state of the art in needle-free valves are known as Luer-Activated Devices. Embodiments of the Luer-Activated Device may control a valve that prevents the outflow of fluid or gas through the connector until a standard luer connector is inserted, allowing the valve to open and fluid to be inserted or withdrawn. Three types of Luer-Activated Devices are known in the art. The first of these are capped Luer-Activated Devices requiring a cap to be attached to the valve when the valve is not in use. These types of devices are difficult to maintain aseptically because contamination can easily occur during manipulation, and the open luer connection is difficult to swab. The second type of Luer-Activated Device is the Capless Luer-Activated Device. Such devices don't require capping between uses and use positive-pressure to open and close the valve when attaching and disconnecting the valve. The third type of Luer-Activated Device is a positive fluid displacement Luer-Activated Device that is similar to the Capless Luer-Activated Device in the means by which they are used, except that they may expel fluid or gas when they are disconnected.

Valves of this nature are typically used in manufacturing sterile medical devices where they hermetically connect two volumes. A common application is the connection between inflation devices and brachytherapy balloons as well as vials, bottles, bags, tubing, needles, and syringes. During the manufacturing of these devices it is often necessary for the outlet and inlet of a valve fitting to communicate so that fluid sterilizing agents reach all surfaces of the device and the volumes they connect. Often times the sterilization procedures are aided by placing the device in a vacuum chamber to assist in drawing fluid sterilization agents into the device through the valve. When used in this manner, the configuration of a luer type device in clinical use differs because it is common for the outlet and inlet to be held closed only permitting the user to develop a differential pressure between the volumes at the outlet and the inlet. In view of this, it is evident that a manufacturer's interests to maintain the valve in an open position does not coincide with the clinician's interests to maintain the valve in a closed position. For example, when the manufacturer attempts to sterilize a closed valve device with a gaseous sterilizing agent, the agent does not reach all of the surfaces of the device. And any vacuum environment used for sterilization will cause an undesired expansion of the volume connected to the fitting outlet, which may ultimately result in the connected volume rupturing and the end user receiving a non-sterile product that may be damaged.

As discussed above, no device exists in the state of the art that compensates for this problem. The present invention solves these and other possible problems of conventional devices, and relates to a passive vent valve or adapter for use with fluid flow and administration structures for medical purposes.

Further, the present invention provides a device that fulfills both the manufacturer's interests as well as the clinician's interests by providing a self contained valve that acts both as a normally open valve during sterilization and normally closed valve during use.

SUMMARY OF DISCLOSURE

In general terms, embodiments of the present invention relate to a valve fitting that comprises a passive vent assembly with a vented body and a luer connection site. The passive vent assembly has a diametrically vented region and a threaded external luer. In the diametrically vented region there are support members that extend between the luer connection site and the threaded external luer. Additionally, the passive vent assembly has a cap that acts as a cover. The internal threads for accepting the threaded external luer within the cap assist in the cap's covering ability. A further aspect of the cap is its ability to be in packaging configuration or use configuration while interfacing with the threaded external luer. To this end, the cap acts as a cover by not substantially overlapping the threaded external valve body in the packaging configuration. However, in the use configuration the cap does substantially overlapping both the vented region and the threaded external luer.

Another embodiment in general terms comprises a brachytherapy kit. Such a kit is made up of a passive vent assembly with a vented body and a luer connection site. The passive vent assembly in the kit has a diametrically vented region and a threaded external luer. In the diametrically vented region there are support members that extend between the luer connection site and the threaded external luer. Additionally, the passive vent assembly has a cap that acts as a cover. The internal threads for accepting the threaded external luer within the cap assist in the cap's covering ability. A further aspect of the cap is its ability to exist in a packaging configuration or use configuration while interfacing with the threaded external luer. To this end, the cap acts as a cover not substantially overlapping the threaded external valve body in the packaging configuration. However, in the use configuration the cap acts as a cover substantially overlapping both the vented region and the threaded external luer. In addition to these components, the kit contains a brachytherapy balloon that comprises a balloon, a catheter shaft, and a brachytherapy port.

Another embodiment of this invention in general terms comprises a method for sterilizing a device. The first step in the method includes providing a passive vent assembly comprising a vented body and a luer connection site. The valve fitting has a diametrically vented region and a threaded external luer. In the diametrically vented region there are support members that extend between the luer connection site and the threaded external luer. Additionally, the passive vent assembly has a cap that acts as a cover. The internal threads for accepting the threaded external luer within the cap assist in the cap's covering ability. A further aspect of the cap is its ability to be in a packaging configuration or a use configuration while interfacing with the threaded external luer. To this end, the cap acts as a cover by not substantially overlapping the threaded external valve body in the packaging configuration. However, in the use configuration the cap acts as a cover substantially overlapping both the vented region and the threaded external luer. Also included with this assembly would be a brachytherapy balloon assembly comprising a balloon, a multi-lumen catheter shaft, and a high-dose-rate brachytherapy port.

The second step of this method includes exposing the passive vent assembly and brachytherapy balloon assembly to a sterilization agent so that the sterilization agent comes into communication with all interior and exterior surfaces of the passive vent assembly, the injection site cap, the balloon, the multi-lumen catheter shaft, and the high-dose-rate brachytherapy port.

The third step of the method then requires maintaining the injection site cap in either the packaging configuration or use configuration while interfacing with the passive vent assembly.

BRIEF DESCRIPTION OF THE DRAWINGS

FIG. 1 provides a representative embodiment of the invention, however, other embodiments of the invention may have differing shapes, sizes and means for connecting brachytherapy devices to other devices, bottles, vials, tubing and inflationary devices.

FIG. 2 provides a representative embodiment of the internal and external layout of the valve body. In other embodiments of the invention, the layout of the device may have differing shapes, sizes and vented regions.

DETAILED DESCRIPTION OF PREFERRED EMBODIMENTS

Figure 1:
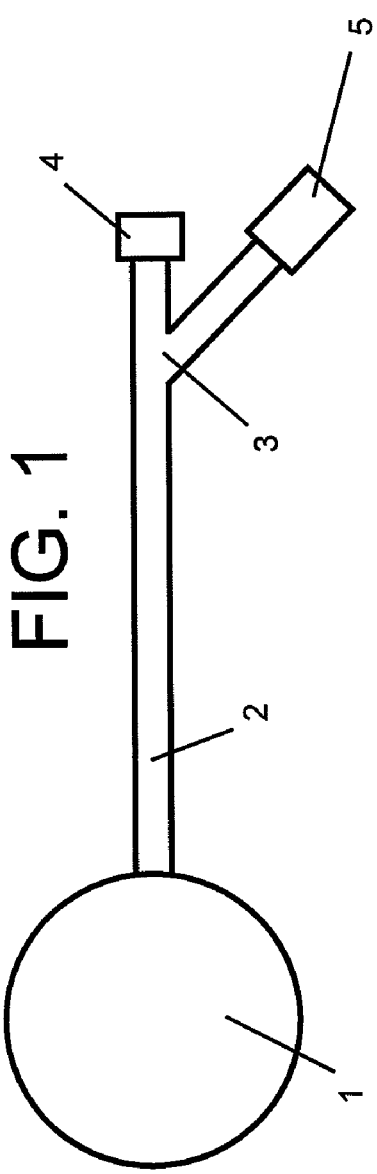
FIG. 1 illustrates a view of one proposed embodiment incorporating a passive vent valve in a brachytherapy device.

Embodiments of the invention are directed to a passive vent assembly having a valve body and cap assembly. The valve body has a connection site at an threaded internal luer end and an threaded external luer end. The valve body defines passageway between the threaded internal luer end and the threaded external luer end. The valve body may internally contain various one-way or two-way valves that make use of diaphragm or actuation like devices known to those of ordinary skill in the art. In addition, encircling the valve body diametrically are multiple open vents between the threaded internal and external luers that provide gaseous passage between the external environment and the internal environment of the valve. In addition, embodiments of the device possess a cap that is slidably disposed around the valve body. The cap comprises captive end and an threaded external injection site interface. The valve body and cap may exist in a packaging configuration and a use configuration. When the cap is in the packaging configuration, it is slidably disposed around the valve body with the threaded external luer end disengaged from the threads in the captive end of the cap. When the collar is in the use configuration, threaded external luer end engages the internal threads of the captive end of the cap.

More specifically, embodiments of the invention are directed to a passive vent assembly having a valve body comprising an threaded internal luer with an optionally inserted male luer connection or other connection device. The valve body also comprises an threaded external luer. Between both of these luers have vented openings placed diametrically around the valve body. Each vented opening contains a vent material that allows the passage of gas, but not liquids. Examples of material that may be used include high-density polyethylene fibers, olefin fibers or polytetrafluoroethylene such as Gore® and Tyvek®. Within the valve body there may be diaphragm devices that act as one and two-way valves and actuation mechanisms in limiting the passage of liquids or gases through the device.

The cap portion of the vented valve possesses a captive end having an overhanging lip at the end of extended length that intersects the internal captive end threads. Beyond the internal captive end threads, is a cap body that may contain valve diaphragm or actuation mechanism that acts as one and two-way valves in limiting the passage of liquids or gases through the device. On the external circumference of the cap body there may be an threaded external injection site interface.

Vented valve assemblies such as these relate to multi-purpose devices that are adaptable to multiple medical use and device requirements. Such devices are suitable for use with brachytherapy balloons, ports, bags, medicine bottles or vials and lock connectors as well as needle free connectors. Other embodiments of the passive vent assembly may be used in obtaining fluids such as diluents for use in reconstituting medications from vials for delivery to ports, other vials, bags, and tubing through use of needle free transfer systems having the adapter valve device in place. Still other embodiments of this device may be used with medical devices that require a connection port that must be closed during use, but open during packaging and sterilization.

Additional embodiments of the invention also generally relate to methods of sterilizing a device using sterilization agents using gases or other flowable materials. Such methods allow for the passage of a sterilization agent through and around all surface areas of the passive vent valve. Specifically, these methods allow the fluid sterilization agent to come in contact with all exposed surface areas that are not limited to, but include the valve body and cap.

Referring now in detail to the figures in which like numerals refer to like or corresponding elements among the five figures. The passive vent valve may be embodied in different configurations and is not limited to any of those configurations disclosed.

Illustrated in FIG. 1 is an embodiment of a brachytherapy device into which the passive vent valve may be incorporated that includes various aspects of the present invention. Other embodiments may have differing shapes, sizes and points of connection. The particular configuration of FIG. 1 as well as all of the figures is for illustration purposes only.

Specifically, FIG. 1 presents an embodiment of a brachytherapy device having a balloon 1 that is positioned at the end of a multi-lumen catheter shaft 2. The catheter shaft 2 bifurcates at a junction 3 into a High Dose Radiation (HDR) port 4. The junction 3, however, may split into multiple lumen or shafts and is not limited to bifurcating. One or more of the lumens after the junction 3 may have a passive vent valve 5 attached.

Figure 2:
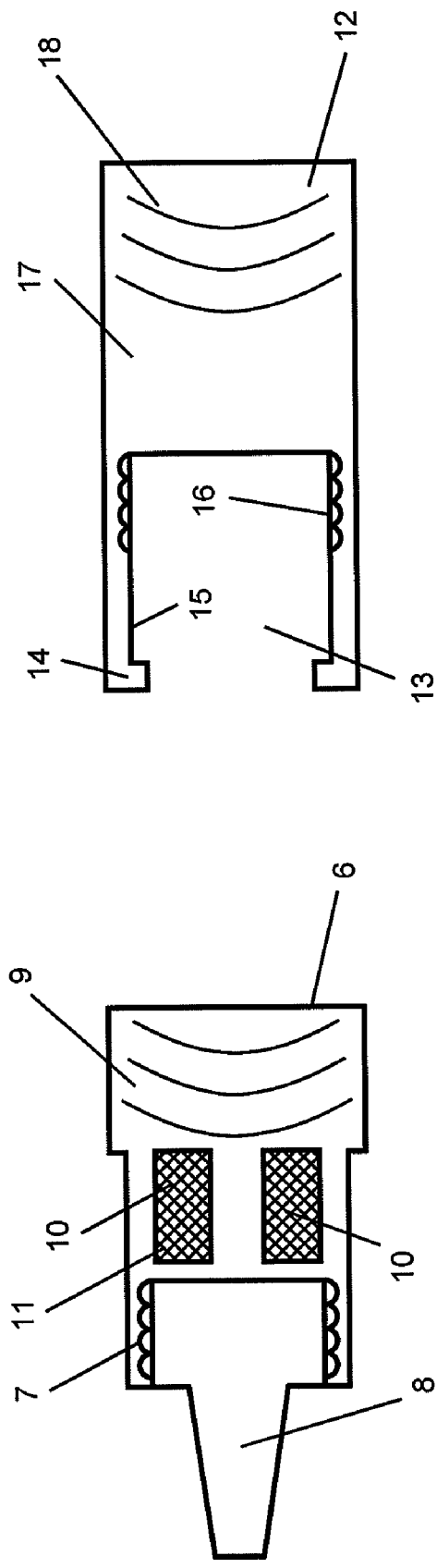
FIG. 2 illustrates a cut away view of one embodiment of a passive vent valve-body.

Illustrated in FIG. 2 is a cut away view of the valve body 6. The valve body consists of a threaded internal luer end 7 that may also comprise other types of interface locking mechanisms in place of, at or near the threaded internal luer end. Within the cavity comprising the threaded internal luer end 7, connection devices such as a male luer 8 may be present for connection to the injection path. Such connection devices comprise many forms that enable the valve body to attach to an injection path of various devices. On the opposite end, the valve body 6 comprises an threaded external luer end 9. The threaded external luer end 9 may also comprise various other means for attaching the valve body 6 to the cap 12 in FIG. 3. Medially spaced between both the threaded internal luer end 7 and the threaded external luer end 9 are vent openings 10 positioned diametrically around the valve body 6. The vent openings 10 are covered in vented mesh materials 11 such as high-density polyethylene fibers, olefin fibers or polytetrafluoroethylene, e.g. Gore® and Tyvek®. All of which may contain specific pore diameters that allow the passage of gas, but not liquid. The vent openings 10 may possess any shape and size depending on the venting needs. The vented mesh material 11 may be attached to the valve body 6 by those means known in the art and may vary depending on the type of vented mesh material 11 incorporated the valve body 6 design. Within the valve body 6, there may be various diaphragm or actuation type devices that limit the flow of liquid or gas through the valve body 6. Such devices include but are not limited to one-way valves and two-way valves. Representative materials from which the valve body 6 is made include: polycarbonate, PVC, acrylic, polypropylene, PET, polytetrafluoroethylene (PTFE), glass-filled PTFE, ethylene polypropylene, flourosilicone, or other thermoplastics known to those of ordinary skill in the art.

Figure 3:
FIG. 3 illustrates a cut away view of one embodiment of the cap on a passive vent valve. Additional representative embodiments of the cap may have differing shapes and sizes.
Figure 4:
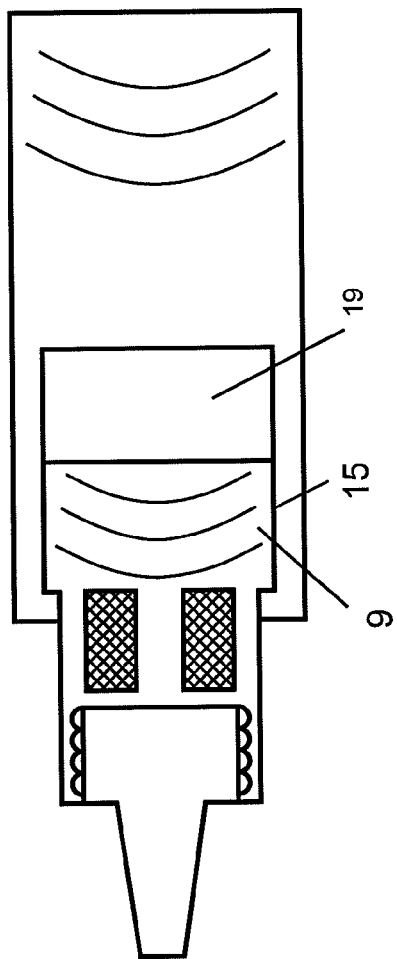
FIG. 4 illustrates a cut away view of one embodiment of a passive vent valve in the packaging configuration. Additional representative embodiments in the packaging configuration may have differing shapes, sizes interlocking mechanisms between the valve body and cap as well as differing interfaces between the valve body and cap of the device.

FIG. 3 illustrates a cut away of the cap 12 portion of the passive vent valve. The cap consists of a captive end 13 for receiving the valve body 6. The captive end of the device possesses and overhanging lip 14 that may be of varying shapes and sizes necessary to secure the valve body to the cap. Extending inside the captive end 13 there is a traversing region 15 in which the valve body 6 is placed when in the packaging configuration as shown in FIG. 4. Further inside the captive end are the internal captive end threads 16 for securing the threaded external luer end 9 of the valve body 6 to the cap 12. In the region of the internal captive threads 16 there may be additional means for securing the valve body 6 to the cap 12 so that valve body and cap may be placed in the use configuration as shown in FIG. 4. Extending further along the cap body 17, the opposite end of the cap 12 possesses an externally threaded injection site interface 18. The region of the externally threaded injection site interface 18 may possess other means known to those of ordinary skill in the art for attaching various devices to the cap 12 and is not limited to a thread-type design. Within the cap body 17, there may be various diaphragm or actuation type devices that limit the flow of liquid or gas through the cap body 17. Such devices include but are not limited to one-way valves and two-way valves. Representative materials from which the cap body 12 is made include: polycarbonate, PVC, acrylic, polypropylene, PET or other thermoplastics known to those of ordinary skill in the art.

FIG. 4 represents the combined valve body and cap in the packaging configuration. In this configuration, the threaded external luer of the valve body 6 is inserted within the captive end 13 of the cap 12. In the packaging configuration, the threaded external luer end 9 of the valve body 6 is positioned at the traversing region 15 of the cap 12 allowing for a space to exist between the threaded external luer end 9 of the valve body 6 and the internal cap end threads 16 of the cap 12. In addition, the overhanging lip 14 of the cap 12 effectively allows the cap 12 to be secured to the valve body 6 thereby inhibiting it from being pulled off or removed.

In the packaging configuration shown in FIG. 4, the diametrically placed vents 10 containing the vented mesh material 11 allow gaseous flow through the valve body 6 contacting all surface areas of the cap 12 and the valve body 6 both internally and externally. Specifically, gaseous flow may enter through the threaded internal luer end 7 or through openings such as the luer connection 8 secured within the threaded internal luer end 7 to internal portions of the passive vent device. In addition, gaseous flow may proceed through the vented mesh material 11 and through the internal portion of the valve body 6 to the open packaging configuration compartment 19. Gaseous flow may also flow through and around the threaded external injection site interface 18 to contact all surface that are exposed.

Figure 5:
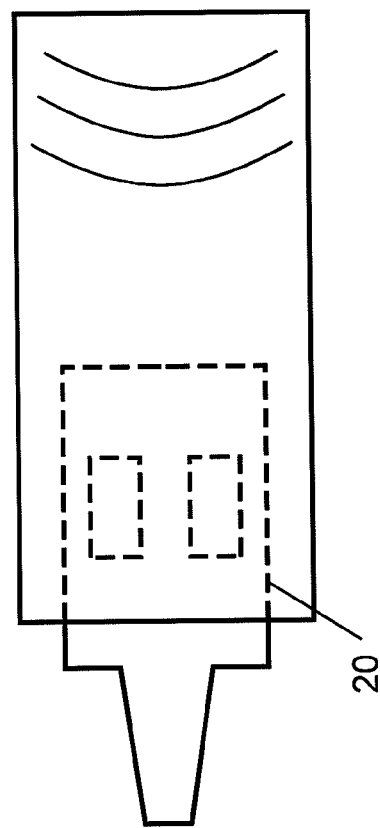
FIG. 5 illustrates a cut away view of one embodiment of a needle-free valve in the use configuration that incorporates aspects of the present invention. Additional embodiments also may conform to the use configuration and result in a differing shape and size of the device.

FIG. 5 represents the combined cap 12 and valve 6 in the use configuration. In this configuration, the threaded external luer end of the valve body 6 is inserted within the captive end 13 of the cap 12. In the use configuration, the threaded external luer end 9 of the valve body 6 is secured to the internal captive end threads 16 of the cap 12 eliminating any space from existing between the threaded external luer end 9 of the valve body 6 and the internal captive end threads 16 of the cap 12. Also in this configuration, the overhanging lip 14 and traversing region 15 of the cap 12 extend over the diametrically placed vented region 10 effectively sealing any gas or liquid from crossing the vented mesh 11. In the use configuration, the overhanging lip 14 and traversing region 15 may extend over the exterior sealing region 20. In order to prevent any flow through the vented mesh 11, should such flow occur, the exterior sealing region 20 may also be coated with or contain materials that ensure a proper seal is made to prevent any leakage between the cap 12 and the valve body 6. These materials include silicon, viton, buna-n, silicone, neoprene, urethane, and other gasket and soft durometer materials known to those of ordinary skill in the art. Further, in the use configuration shown in FIG. 5, the diametrically placed vents 10 containing the vented mesh material 11 are covered by the overhanging lip 14 and the traversing region 15 creating a sealed system functioning as a one-way or two-way valve or actuation device.

Preferred embodiments include a passive vent assembly wherein the vented region is interspersed with support members that comprise multiple individual vents. In these embodiments, the vents comprise a fluid impermeable membrane that is made up of high density polyethylene fibers, olefin fibers or poly tetrafluoroethylene. Each of the materials making up the vents have pore sizes of 0.1 micron and larger. In addition, the preferred embodiments of this invention possess a male luer connection on the valve body.

An additional embodiment of the invention includes a method of sterilizing a device. In this method, sterilizing gas passes around the exterior of the device and through the vented mesh material 11, through the male luer connection 8 or opening present where the male luer connection would be inserted, and through the opening located internally to the threaded external injection site interface 18. Once the gas passes into and around the exterior of the device. All of the surface areas exposed to the gas are then sterilized both internally and externally.

Methods such as those encompassed by embodiments of the claimed invention make use of ethylene oxide as a sterilization agent. However, additional means of gas sterilization use plasma/hydrogen peroxide gas, ozone and chlorine dioxide. While other methods of sterilization include radiation and e-beam processes, pulsed UV light, x-ray and gamma irradiation, electron beam, steam and heat processes, autoclaves and dry heat. Each of which may be combined or performed separately.

The use of ethylene oxide is the state of the art in sterilizing devices. The relatively low process temperature (in comparison to steam sterilization) has made ethylene oxide an excellent means for sterilizing many products.

The methylating properties of ethylene oxide makes it an ideal sterilizing agent. This property, however, also makes it extremely dangerous at ambient oxygen levels. To ensure an intrinsically safe environment for the ethylene oxide, a set of evacuations coupled with steam additions is executed at the start of every sterilization procedure. Ethylene oxide gas is then added and allowed to sit with the product being sterilized. During this point in the method, the ethylene oxide comes in contact with all of the surface areas of the passive vent assembly. During this "sitting phase" or "gas dwell phase" the product and its packaging absorb ethylene oxide gas. Following the gas dwell phase, a series of evacuations and air infusions occur. This helps in the removal of gas from the product. The product is then transferred to an aeration chamber where ethylene oxide and ethylene oxide degradation products dissipate safely from the product. Depending on the nature of the product and aeration conditions, this gas dissipation period may last from several hours to weeks and even months. When sterilization is complete, the gas is evacuated from the chamber and the product is removed.

In the present invention, the preferred embodiment of the method uses ethylene oxide gas for sterilizing the device.

A person skilled in the art will appreciate the foregoing as only illustrative of the principles of the invention, and that various modification may be to both the device and the methods of sterilizing the device presented without departing from the scope and spirit of the invention.

What is claimed is:

1. A brachytherapy kit, said kit comprising:
a vent assembly comprising a venting body and a cap;
said venting body comprising a diametrically vented region and a threaded external luer;
said cap comprising internal threads for accepting said threaded external luer, wherein said cap has a use configuration and a packaging configuration wherein said cap substantially overlaps said vented region when in the use configuration, and wherein said cap does not substantially overlap said vented region when in the packaging configuration; and
a brachytherapy balloon assembly comprising a balloon, a catheter shaft, and a brachytherapy port, wherein said vent assembly is attached to said brachytherapy balloon assembly;
wherein said cap is configured in the packaging configuration to allow gaseous flow through said venting body to be in fluid communication with substantially all interior and exterior surface areas of said kit.

2. The brachytherapy kit of claim 1, wherein said diametrically vented region comprises multiple individual vents.

3. The brachytherapy kit of claim 2, wherein said vents comprise high-density polyethylene fibers, olefin fibers or polytetrafluoroethylene.

4. The brachytherapy kit of claim 2, wherein said vents comprise a fluid impermeable membrane.

5. The brachytherapy kit of claim 4, wherein said fluid impermeable membrane comprises a pore size greater than 0.1 micron.

6. The brachytherapy kit of claim 4, wherein said fluid impermeable membrane allows the passage of ethylene oxide gas.

7. The brachytherapy kit of claim 4, wherein said membrane comprises high-density polyethylene fibers, olefin fibers or polytetrafluoroethylene.

8. The brachytherapy kit of claim 1, wherein said venting body further comprises a threaded internal luer.

9. The brachytherapy kit of claim 8, wherein said threaded internal luer comprises a male luer connection.

10. The brachytherapy kit of claim 1, wherein said diametrically vented region comprises a one-way valve.

11. The brachytherapy kit of claim 1, wherein said diametrically vented region comprises a two-way valve.

12. The brachytherapy kit of claim 1, wherein said cap comprises a captive end for receiving the venting body.

13. The brachytherapy kit of claim 12, wherein said captive end comprises an overhanging lip.

14. A brachytherapy kit, said kit comprising:
a vent assembly comprising a venting body and a cap;
said body comprising a vent and an external luer;
said cap configured to accept said external luer, wherein said cap has a use configuration and a packaging configuration wherein said cap substantially overlaps said vent when in the use configuration, and wherein said cap does not substantially overlap said vent when in the packaging configuration;
a catheter shaft; and a brachytherapy balloon attached to an end of said catheter shaft, wherein said vent assembly is attached to said catheter shaft;

wherein said cap is configured in the packaging configuration to allow gaseous flow through said body to be in fluid communication with substantially all interior and exterior surface areas of said kit.

15. The brachytherapy kit of claim 14, wherein said vent assembly further comprises a one-way valve.

16. The brachytherapy kit of claim 14, wherein said vent assembly further comprises a two-way valve.

17. The brachytherapy kit of claim 14, wherein said vent comprises a fluid impermeable membrane.

18. The brachytherapy kit of claim 14, wherein said cap comprises a captive end for receiving said body.

19. The brachytherapy kit of claim 18, wherein said captive end comprises an overhanging lip.

\* \* \* \* \*